United States Patent [19]

Young et al.

[11] Patent Number: 5,104,899
[45] Date of Patent: Apr. 14, 1992

[54] METHODS AND COMPOSITIONS FOR TREATING DEPRESSION USING OPTICALLY PURE FLUOXETINE

[75] Inventors: James W. Young, Still River; Timothy J. Barberich, Concord, both of Mass.

[73] Assignee: Sepracor, Inc., Marlborough, Mass.

[21] Appl. No.: 566,655

[22] Filed: Aug. 13, 1990

[51] Int. Cl.$^5$ ............................................. A61K 31/13
[52] U.S. Cl. ..................................................... 514/646
[58] Field of Search ........................................ 514/646

[56] References Cited

U.S. PATENT DOCUMENTS

| | | | |
|---|---|---|---|
| 3,536,809 | 10/1970 | Applezweig | 514/646 |
| 3,598,123 | 8/1971 | Zeffaroni | 514/646 |
| 3,630,200 | 6/1969 | Higuchi | 514/646 |
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 128/260 |
| 4,018,895 | 4/1977 | Molloy et al. | 514/646 |
| 4,194,009 | 3/1990 | Molloy et al. | 514/646 |
| 4,329,356 | 5/1982 | Holland | 514/646 |
| 4,444,778 | 4/1984 | Coughlin | 514/252 |
| 4,590,213 | 5/1986 | Stark | 514/646 |
| 4,594,358 | 6/1986 | Hynes | 514/651 |
| 4,596,807 | 6/1986 | Crosby | 514/277 |
| 4,626,549 | 12/1986 | Molloy et al. | 514/651 |
| 4,647,591 | 3/1987 | Cherkin et al. | 514/651 |
| 4,698,342 | 10/1987 | Crosby | 514/253 |
| 4,777,173 | 10/1988 | Shrotryia et al. | 514/252 |
| 4,797,286 | 1/1989 | Thakker et al. | 514/200 |
| 4,847,092 | 7/1989 | Thakker et al. | 514/200 |
| 4,868,344 | 9/1989 | Brown | 514/646 |
| 4,895,845 | 1/1990 | Seed | 514/252 |
| 4,918,207 | 4/1990 | Brown | 549/504 |
| 4,918,242 | 4/1990 | Brown | 549/504 |
| 4,918,246 | 4/1990 | Brown | 549/504 |

FOREIGN PATENT DOCUMENTS 8830930.7  4/1988  European Pat. Off. .
88/03709  5/1989  PCT Int'l Appl. .

OTHER PUBLICATIONS

Wong et al., *Acta Pharm. Nord.* 2(3): 171-180 (1990).
Caccia et al., *Psychopharmacology* 100: 509-514 (1990).
Benfield et al., *Drugs* 32: 481-508 (1986).
Coutts, et al., *Chirality*, 1: 99-120 (1989).
Coutts, et al., *Prog. Neuro-Psychopharmacol. and Biol. Psychiat.*, 13: 405-417 (1989).
Robertson, et al., *J. Med. Chem.*, 31: 1412-1417 (1988).
Corey et al., *Tetrahedron Lett.*, 30:(39) 5207-5210 (1989).
Teicher, et al., *Am. J. Psychiatry*, 147(2): 207-210 )1990).
Scip's New Product Review, No. 7: 13-14 (1986).
Gao, et al., *J. Org. Chem.*, 53(17): 4081-4084 (1988).
Bremmer, *J. Clin. Psychiatry*, 45(10): 414-420 (1984).
Wong, et al., *Pharmacology, Biochemistry and Behavior*, 31: 475-479 (1988).
Fuller, et al., *Pharmacology, Biochemistry and Behavior*, 24: 281-284 (1986).
Wong, et al., *Drug Development Research*, 6: 397-403 (1985).
Kim et al., *Physiology & Behavior*, vol. 42: 319-322 (1988).
Chem. Abst 112 (1990)—216327e.

*Primary Examiner*—S. J. Friedman
*Attorney, Agent, or Firm*—Pennie & Edmonds

[57] ABSTRACT

A method and composition are disclosed utilizing the pure S(+) isomer of fluoxetine, which is a potent antidepressant substantially free of adverse toxic or psychological effects, having a rapid onset of action and a high response rate.

13 Claims, No Drawings

METHODS AND COMPOSITIONS FOR TREATING DEPRESSION USING OPTICALLY PURE FLUOXETINE

BACKGROUND OF THE INVENTION

This invention relates to a novel composition of matter which possesses potent antidepressant activity as a serotonin uptake inhibitor while avoiding the usual detrimental factors, unwanted effects and adverse toxic or psychological effects associated with such agents. Also disclosed are methods of using said composition to treat depression while avoiding the usual detrimental factors, unwanted effects, and side effects associated with such agents.

The active compound of this composition and method is an optical isomer of the compound fluoxetine which is described in U.S. Pat. Nos. 4,018,895 and 4,194,009 to Molloy, et al. Chemically this isomer is (+)N-methyl-3-phenyl-3-[($\alpha,\alpha,\alpha$-trifluoro-p-tolyl)-oxy]-propylamine, herein after referred to as S(+) fluoxetine.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (−) or d and l are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of propranolol, which is known to be 100 times more potent than the D-enantiomer.

Furthermore, optical purity is important since certain isomers may actually be deleterious rather than simply inert. For example, the D-enantiomer of thalidomide was a safe and effective sedative when prescribed for the control of morning sickness during pregnancy. However, its L-thalidomide counterpart was discovered to be a potent teratogen.

Fluoxetine (Prozac ®), which is the subject of the present invention, is available only as a racemic mixture. That is, it is a mixture of optical isomers, called enantiomers.

The racemic mixture of fluoxetine, in addition to its use as an antidepressant, has been shown to have a wide spectrum of action which includes:
Treatment of diabetes (EPA 88303930.7)
Assisting in weight loss (appetite suppression) (U.S. Pat. No. 4,895,845)
Treatment of alcohol abuse (U.S. Pat. No. 4,777,173)
Analgesia - control of pain (U.S. Pat. Nos. 4,698,342 and 4,594,358)
Treatment of atherosclerosis (U.S. Pat. No. 4,444,778)
Improvement of memory (U.S. Pat. No. 4,647,591)
Treatment of anxiety (U.S. Pat. No. 4,590,213)
Treatment of hypertension (U.S. Pat. No. 4,329,356)

Whereas the foregoing Molloy et al. patents, in addition to the above discussed European patent application and U.S. patents, recognize compounds such as fluoxetine have optically active forms, no example of an optically active form is given. Furthermore, prior art studies with the enantiomers of fluoxetine have generally concluded the fluoxetine enantiomers are equipotent and that there is no advantage in the use of the pure S-enantiomer. See, Robertson et al., *J. Med. Chem.*, 31: pg. 1412-1417 (1988). However, it has now been discovered that there are indeed unforeseen advantages in the use of the pure S-enantiomer of fluoxetine.

Fluoxetine is used in the treatment of depression, which along with mania falls under the heading of affective disorders. Mania and depression are characterized by changes in mood as the primary symptom. Either of these two extremes of mood may be accompanied by psychosis with disordered thought and delusional perceptions. Psychosis may have, as a secondary symptom, a change in mood, and it is this overlap with depression that causes much confusion in diagnosis. Severe mood changes without psychosis frequently occur in depression and are often accompanied by anxiety. Depression is characterized by feelings of intense sadness or pessimistic worry, agitation, self-deprecation, physical changes (including insomnia, anorexia, and loss of drive, enthusiasm, and libido), and mental slowing. Among the more common treatments for depression are the administration of a tricyclic antidepressant agent.

Fluoxetine is not in the class of drugs known as tricyclic antidepressants. Its antidepressant action is presumed to be based on its highly specific inhibition of serotonin uptake in serotoninergic neurons in the brain. It is also chemically unrelated to tetracyclic or other available antidepressant agents.

Fluoxetine has certain advantages over other antidepressant drugs. Antagonism of muscarinic, histaminergic and $\alpha_1$ adrenergic receptors has been hypothesized to be associated with various anticholinergic and cardiovascular effects of classical tricyclic antidepressant drugs. Fluoxetine binds to these and other membrane receptors from brain tissue much less potently than do these tricyclic antidepressants. Thus, fluoxetine gives less anticholinergic side effects such as blurred vision, dry mouth, constipation and urinary retention. There is also less lowering of blood pressure, tachycardia and arrhythmias.

While fluoxetine has certain advantages, it also has disadvantages. Among these disadvantages are side effects other than the ones described above. The most frequent reported side effects associated with fluoxetine are headaches, nervousness, anxiety and insomnia. These are reported by 10% to 15% of patients treated with fluoxetine. These symptoms led to drug discontinuation in 5% of the patients treated with the drug. It is also known that in some patients use of fluoxetine is associated with severe anxiety leading to intense violent suicidal thoughts. Teicher et al., *Am. J. Psychiatry*, 147:2 pg. 207-210 (1990). In other patients manic behavior follows treatment with fluoxetine. Other side effects associated with fluoxetine include nausea, diarrhea and drowsiness.

Another disadvantage of fluoxetine is its long half-life and the concominant delay in onset of action. The half-life of fluoxetine is approximately 2 to 3 days. Steady state plasma concentrations are achieved only after continuous dosing for weeks.

A further disadvantage of fluoxetine is that it has a low response rate. Overall, 44% of the patients being treated with fluoxetine showed antidepressant effect. In patients who had not previously responded to other anti-depressant therapy the response to fluoxetine was 43%. In addition, in patients with no previous treatment with anti-depressants, or with a history of good response to previous treatment, response to fluoxetine was 56%. (Scrip's New Product Review, pages 13–14, 1986).

Another disadvantage of fluoxetine is that in addition to its use as an antidepressant it has other activity such as severe appetite suppression, drowsiness, analgesia and hypotension. These other activities may be unwanted effects when treating a patient suffering from depression.

It is therefore desirable to find a compound with the advantages of fluoxetine which would not have the above described disadvantages.

SUMMARY OF THE INVENTION

It has now been discovered that the S(+) isomer of fluoxetine does not have certain side effects, including causing nervousness, anxiety, insomnia, and adverse psychological effects; has a fast onset of action and an increased response rate. It has also been discovered that with the use of the S(+) isomer of fluoxetine it is possible to avoid other activities of the racemic compound which would be unwanted effects when treating a patient suffering from depression. Thus, the S(+) isomer of fluoxetine is useful for methods of treating depression and in the compositions used thereof where these detrimental effects will be avoided.

DETAILED DESCRIPTION OF THE INVENTION

The present invention encompasses a method of eliciting an antidepressant effect while avoiding the concomitant liability of adverse toxic or psychological effects, delayed onset of action or low response rate associated with a racemic mixture which comprises administering to a patient in need of antidepressant therapy an amount sufficient to alleviate human depression, but insufficient to cause said adverse toxic or psychological effects, delayed onset of action and low response rate, of S(+) fluoxetine or a pharmaceutically acceptable salt thereof, substantially free of its R(−) stereoisomer.

The present invention further encompasses a method of eliciting an antidepressant effect while avoiding unwanted effects, which comprises administering to a patient in need of antidepressant therapy an amount sufficient to alleviate a human,s depression, but insufficient to cause said unwanted effects, of S(+) fluoxetine or a pharmaceutically acceptable salt thereof, substantially free of its R(−) stereoisomer.

The present invention also encompasses an antidepressant composition for the treatment of a patient in need of antidepressant therapy which comprises an amount sufficient to alleviate the depression but insufficient to cause adverse toxic or psychological effects, delayed onset of action and low response rate, of S(+) fluoxetine or a pharmaceutically acceptable salt thereof, substantially free of its R(−) stereoisomer.

Also embodied in the present invention is an antidepressant composition adapted for the treatment of a patient in need of antidepressant therapy which comprises an amount sufficient to alleviate the depression but insufficient to cause unwanted effects, of S(+) fluoxetine or a pharmaceutically acceptable salt thereof, substantially free of its R(−) stereoisomer.

The racemic mixture of fluoxetine (i.e., a mixture of R and S stereoisomers) has antidepressant effect; however this racemic mixture causes adverse toxic or psychological effects, has a delayed onset of action, and has a low response rate. The S(+) isomer of fluoxetine does not cause these adverse toxic or psychological effects, has a rapid onset of action and has a high response rate. Thus, it is much more desirable to use the S(+) isomer of fluoxetine.

Furthermore, although there is some variability from one patient to another, it is generally observed that, by administering an effective amount of only the S(+) isomer of fluoxetine it is possible to accomplished a more "targeted" therapy. A more "targeted" therapy means that by using the S(+)isomer of fluoxetine the compounds broad activity can be taken advantage of without also having unwanted effects. This is important since it is not desirable for all patients to be administered a compound with such a complex and multifaceted spectrum of activity. The term "unwanted effects" includes but is not limited to (1) severe appetite suppression; (2) drowsiness or analgesia; and (3) hypotension. Thus by administering to a patient the S(+)isomer of fluoxetine, significant antidepressant activity is obtained without the above identified unwanted effects which are associated with the racemic mixture of fluoxetine.

The term "adverse toxic or psychological effects" includes but is not limited to headaches, nervousness, anxiety, insomnia, nausea, diarrhea, drowsiness, intense violent suicidal thoughts and manic behavior.

The term "substantially free of the R(−) stereoisomer" as used herein means that the composition contains at least 90% by weight of S(+) fluoxetine and 10% by weight or less of R(−) fluoxetine. In the most preferred embodiment the term "substantially free of the R(−) stereoisomer" means that the composition contains at least 99% by weight S(+) fluoxetine and 1% or less of R(−) fluoxetine.

The term "eliciting an antidepressant effect" means relief from the symptoms associated with depression, which include but are not limited to feelings of intense sadness or pessimistic worry, agitation, self-deprecation, physical changes (including insomnia, anorexia, and loss of drive, enthusiasm and libido) and mental slowing.

The synthesis of the (+) or (−) isomer of fluoxetine can be performed by two methods which are as follows:

METHOD 1

This method is disclosed in Gao, et al. *J. Org. Chem.* Vol. 53, No. 17, pp. 4081–4084 (1988). It involves the use of 1-phenyl-1,3-propanediols, which are key intermediates. The 1-phenyl-1,3-propanediols are prepared from cinnamyl epoxy alcohols by Red - AL reduction. The chiral cinnamyl epoxy alchols are made by, asymmetric epoxidation of cinnamyl alcohols as disclosed in Gao, et al.

The reaction scheme is as follows:

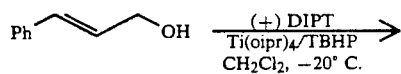

-continued

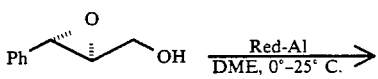
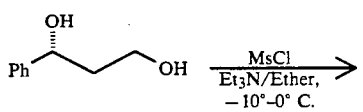
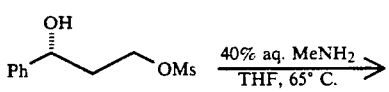
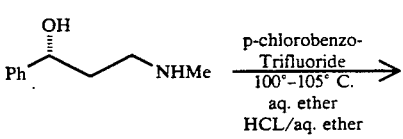
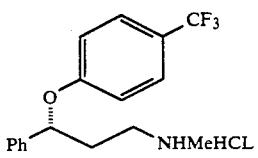

(R)-(−)-Fluoxetine hydrochloride (S)-(+) fluoxethine hydrochloride is prepared from (2R) - Epoxycinnamyl alcohol obtained by the asymmetric epoxidation disclosed in Gao et al. utilizing (−)-DIPT.

METHOD 2

This method is based on the asymmetric reduction of ketone with chiral borane reagent as disclosed in U.S. Pat. No. 4,868,344 to H. C. Brown.

The reaction scheme is as follows:

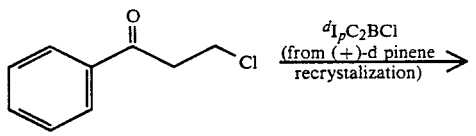
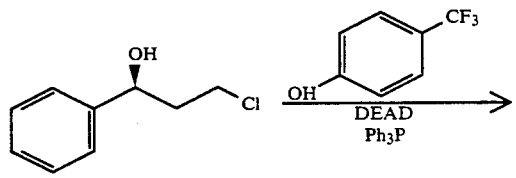
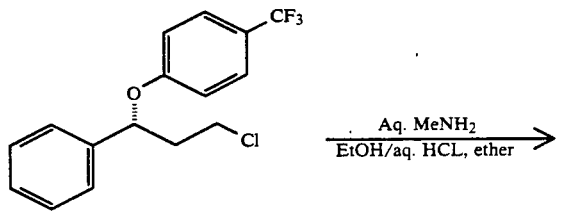
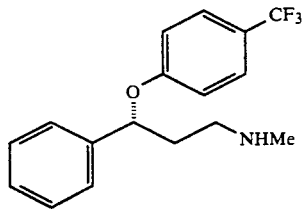

The magnitude of a prophylactic or therapeutic dose of S(+) fluoxetine will, of course, vary with the nature of the severity of the condition to be treated and its route of administration. It will also vary according to the age, weight and response of the individual patient. In general, the daily dose range for anti-depressant use lie within the range of from about 5 mg to about 100 mg per day, preferably 20 mg to 80 mg per day, and most preferably from about 40 mg to 80 mg per day, in single or divided doses. On the other hand, it may be necessary to use dosages outside these limits in some cases. The term "an amount sufficient to alleviate a human's depression but insufficient to cause said adverse toxic or psychological effects, delayed onset of action or low response rate" is encompassed by the above-described amounts.

Any suitable route of administration may be employed for providing the patient with an effective dosage of S(+) fluoxetine. For example, oral, rectal, parenteral, transdermal, subcutaneous, intramuscular, inhalation and the like may be employed. Dosage forms include tablets, troches, dispersions, suspensions, solutions, capsules, patches and the like.

The pharmaceutical compositions of the present invention comprise S(+) fluoxetine as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic acids including inorganic acids and organic acids.

Since the compound of the present invention is basic, salts may be prepared from pharmaceutically acceptable non-toxic acids, including inorganic and organic acids. Such acids include acetic, benzene-sulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Particularly preferred are hydrobromic, hydrochloric, phosphoric and sulfuric acids.

The compositions include compositions suitable for oral, rectal, parenteral (including subcutaneous, intramuscular, and intravenous), although the most suitable route in any given case will depend on the nature and severity of the condition being treated. The most preferred route of the present invention is oral. They may be conveniently presented in unit dosage form and prepared by any of the methods well-known in the art of pharmacy.

In the case where an oral composition is employed, a suitable dosage range for use is, e.g., from about 5 mg to about 100 mg of fluoxetine per day, preferably from about 20 mg to about 80 mg per day and most preferably from about 40 mg to about 80 mg per day.

In practical use, S(+) fluoxetine can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. The most preferred solid oral preparation is capsules. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference. The use of a racemic mixture of fluoxetine in a sustained release formulation is disclosed and/or claimed in U.S. Pat. Nos. 4,797,286 and 4,847,092.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binner, lubricant, inert diluent, surface active or dispersing agent. Molded tablets may be made by molding in a suitable machine, a mixture of the powdered compound moistened with an inert liquid diluent. Desirably, each tablet contains from about 5 mg to about 100 mg of the active ingredient and each cachet or capsule contains from about 5 to about 100 mg of the active ingredient. Most preferably the tablet, cachet or capsule contains 20 mg of active ingredient.

The invention is further defined by reference to the following examples describing in detail the preparation of the compound and compositions of the present invention. It will be apparent to those skilled in the art that many modifications, both to materials and methods, may be practiced without departing from the purpose and interest of this invention.

All temperatures are in degrees Celsius.

EXAMPLES

Example 1

Synthesis of R(−) and S(+) Fluoxetine

Reduction of epoxycinnamyl alcohols with Red-Al; synthesis of fluoxetine

Part 1

(R)-3-Phenyl-1,3-dihydroxypropane

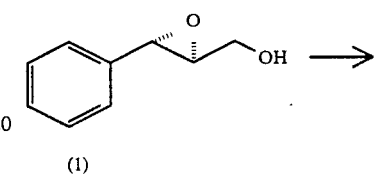

(1)

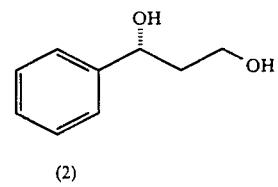

(2)

To a solution of (−)-(2S,3S)-epoxycinnamyl alcohol 1) (1.5 g, 10.0 mmol) (synthesized by the method disclosed in Gao et al., *J. Org. Chem.*, Vol. 53, No. 17, ppg 4081-4084 (1988).), in dimethoxyethane (50 mL) was added a 3.4 molar solution of REd-Al in toluene (3.1 mL, 10.5 mmol) dropwise under nitrogen at 0° C. After stirring at room temperature for three hours, the solution was diluted with ether and quenched with 5% HCl solution. After stirring at room temperature for 30 min, the resulting white precipitate formed was filtered and boiled with ethyl acetate and filtered again. The combined organic solutions were dried with magnesium sulfate. Concentration gave (R)-3-phenyl-1,3-dihydroxypropane (2) as a slightly yellow oil which was used without further purfication (1.5 g, 98%): $^1$H NMR (CDCl$_3$) &7.2–7.3 (m, 5H), 4.88–4.98 (m, 1H), 3.78–3.86(t, J=7.5 Hz, 2), 3.3–3.4 (br. s, 1H), 2.85–2.95 (br. s, 1H), 1.84–2.08 (m, 2H); the ratio of 1,3-diol to 1,2-diol was 20:1 by $^1$H NMR analysis of the derived diacetate.

(S)-3-Phenyl-1,3-dihydroxypropane (2) was prepared according to the above procedure starting with 300 mg of (+)-epoxycinnamyl alcohol to provide 300 mg of (S)-3-phenyl-1,3-dihydroxypropane (1,3-diol:1,2-diol=21:1).

Part 2

(S)-3-phenyl-3-hydroxypropyl-1-methanesulfonate

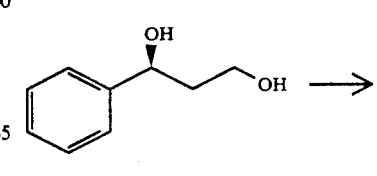

(3)

-continued

To a solution of (S)-3-phenyl-1,3-dihydroxypropane (3) (2.71 g, 17.8 mmol) and triethylamine (2.60 g, 25.6 mmol) in ether (90 mL) was added dropwise MsCl (1.45 mL, 18.7 mmol) under nitrogen at −10° C. After stirring at −10° C. to 0° C. for 3 h, the mixture was poured into ice water (30 mL) and washed with 20% H$_2$SO$_4$, saturated aqueous NaHCO$_3$, brine, and dried over magnesium sulfate. The crude products were purified by chromatography eluting with 45% ethyl acetate in hexane to give the title compound (4) as an oil (3.50 g, 85%): $^1$H NMR (CDCl$_3$ &7.3–7.4 (m, 5H), 4.85–4.91 (t, J=7.7 Hz, 1H), 4.42–4.52 (m, 1H), 4.22–4.32 (m, 1H), 3.0 (s, 3H), 2.3 (s, 1H), 2.1–2.2 (q, J=7.7 Hz, 2H).

(R)-3-Phenyl-3-hydroxypropyl-1-methanesulfonate was prepared from (R)-3-phenyl-1,3-dihydroxypropane by the above procedure in 74% yield.

These two compounds were either stored at 0° C. or used soon after preparation.

Part 3
(S)-N-Methyl-3-phenyl-3-hydrpoxypropylamine

A solution of (S)-3-phenyl-3-hydroxypropyl-1-methanesulfonate (5) (690 mg, 3.0 mmol) and methylamine (10 mL, 40% in water) in THF (10 mL) was heated at 65° C. for 3 h. After cooling, the solution was diluted with ether and washed with saturated aqueous sodium bicarbonate, brine, and dried with anhydrous potassium carbonate. Concentration to dryness provided the title compound (6) (476 mg, 96%): $^1$H NMR (CDCl$_3$) δ7.2–7.4 (m, 5H), 4.94 (dd, J=3.8, 7.2 Hz, 1H), 3.4–3.9 (br. s, 1H), 2.84–2.92 (m, 2H), 2.45 (s, 3H), 1.68–1.92 (m, 3H).

Following a procedure identical to the above 1.15 g (R)-3-phenyl-3-hydroxypropyl-1-methanesulfonate yielded 837 mg of (R)-N-methyl-3-phenyl-3-hydroxypropylamine.

Part 4
(R)-Fluoxetine hydrochloride

To a solution of (R)-N-methyl-3-phenyl-3-hydroxypropylamine (7) (1.23 g, 7.45 mmol) in dimethyl acetamide (7 mL) was added sodium hydride (215 mg, 8.95 mmol) with cooling. The mixture was heated at 90° C. for 1.5 h, and an orange solution resulted. To this solution was then added 4-chlorobenzotrifluoride (3.23 g, 2.40 mL, 17.9 mmol), and the mixture was heated at 100°–105° C. for 2.5 h. After cooling and dilution with toluene, the mixture was washed with water, and the aqueous layer was separated and extracted with toluene. The combined toluene solutions were then washed with saturated aqueous sodium bicarbonate, brine, and dried over magnesium sulfate. Concentration provided (R)-fluoxetine as an orange oil (1.97 g, 86%). The oil was dissolved in ether and acidified with hydrogen chloride gas (pH=3–4) to give a acidic ethereal solution (no precipitate formed). The solution was concentrated at room temperature to give a yellow solid which was washed with ether to remove most of the orange color. The slightly yellow solid was then recrystallized from acetonitrile at −20° C. The solid was collected and washed with ether to provide (R)-fluoxetine hydrochloride (s) as a white powder (1.90 g, 75%): mp 140°–142° C. (lit.$^{133b}$mp 140°–141.5° C.; [α]$^{23}$D-2.16. (c 1.62, MeOH); (lit.$^{133b}$ [α]$^{23}$D-1.97° [c 1.00, MeOH]); [α]$^{23}$D+7.08. (c 1.30, H$_2$O); (lit. [α]$^{23}$D+10.32° [c 1.00, H$_2$O]); IR (KBr, CDCl$_3$ 2950, 2640, 2450, 1620, 1595, 1520, 1360, 1250, 1180, 1170, 1130, 1114, 1070, 840 cm-1; $^1$H NMR (CDCl$_3$) & 9.72 (br, s, 2H), 7.40–7.43 (d, J=8.7 Hz, 2H), 7.25–7.33 (m, 5H), 6.88–6.92 (d, J=8.7 Hz, 2H), 5.45–5.50 (dd, J=4.6, 7.9 Hz, 1H), 3.12 (br, s, 2H), 2.55–2.62 (br, s, 3H), 2.42–2.52 (m, 2H); Anal. Calcd. for C$_{17}$H$_{19}$ClF$_3$NO: C, 59.05; H, 5.54; N, 4.05; F, 16.48; Cl, 10.25. Found: C, 58.84; H, 5.55; N, 3.94; F, 16.28; Cl, 10.50.

(S)-Fluoxetine hydrochloride was prepared by the above procedure from (S)-N-methyl-3-phenyl-3-hydroxypropylamine: mp 140°–142° C. (lit$^{133b}$ mp 135°–137° C.); [α]$^{23}$D -7.12° (c 1.53, H$_2$O); lit$^{133b}$ [α]$^{23}$D -10.85° [c 1.00, H$_2$O]); Anal. Calcd. for C$_{17}$H$_{19}$ClF$_3$NO: C, 59.05; H, 5.54; N, 4.05. Found: C, 59.19; H, 5.42; N, 3.89.

EXAMPLE 2

Oral Formulation

| Capsules: | |
|---|---|
| Formula | Quantity per Capsule (Mg.) |
| Active ingredient | 20.00 |
| Lactose | 55.75 |
| Corn Starch | 18.75 |
| Magnesium Stearate | 0.50 |
| | 125.00 |

Blend the active ingredient, lactose and corn starch until uniform; then blend the magnesium stearate into the resulting powder, Encapsulate the mixture into suitably sized two-piece hard gelatin capsules.

EXAMPLE 3

Oral Formulation

| Tablets: | |
|---|---|
| Formula | Quantity per Tablet |
| Active Ingredient | 20.00 |
| Lactose | 52.75 |
| Corn Starch | 3.0 |
| Water (per thousand Tablets) | 30.0 ml* |
| Corn Starch | 18.75 |
| Magnesium Stearate | 0.5 |
| | 125.00 |

*The water evaporates during manufacture

Blend the active ingredient with the lactose until uniform. Blend the smaller quantity of cornstarch with the water and add the resulting corn starch paste, then mix until a uniform wet mass is formed. Add the remaining corn starch to the resulting wet mass and mix until uniform granules are obtained. Screen the granules through a suitable milling machine, using a ¼ inch stainless steel screen. Dry the milled granules in a suitable drying oven until the desired moisture content is obtained. Mill the dried granules through a suitable milling machine using ¼ mesh stainless steel screen. Blend in the magnesium stearate and compress the resulting mixture into tablets of desired shape, thickness, hardness and disintegration.

What is claimed is:

1. A method of eliciting an antidepressant effect while avoiding concomitant liability of adverse toxic or physiological effects, delayed onset of action or low response rate, which comprisesd administering to a patient in need of antidepressant therapy an amount sufficient to alleviate human depression, but insufficient to cause said adverse toxic or psychological effects, delayed onset of action or low response rate, of S(+) fluoxetine or a pharmaceutically acceptable salt thereof, substantially free of its R(−) stereoisomer.

2. The method of claim 1 wherein the amount administered is 5 mg to 100 mg per day.

3. The method according to claim 2 wherein the amount administered is 40 mg to 80 mg per day.

4. The method according to claim wherein the amount of S(+) fluoxetine or a pharmaceutically acceptable salt thereof is greater than approximately 99% by weight.

5. The method according to claim 1 wherein S(+) substantially free of its R(−) stereoisomer is administered together with a pharmaceutically acceptable carrier.

6. A method according to claim 2 wherein S(+) flouxetine hydrochloride is administered.

7. A method of eliciting an antidepressant effect while avoiding unwanted effects which comprises administering to a patient in need of antidepressant therapy an amount sufficient to alleviate human depression, but insufficient to cause said unwanted effects, of S(+) fluoxetine or a pharmaceutically acceptable salt thereof, substantially free of its R(−) stereoisomer.

8. The method of claim 7 wherein the unwanted effects are severe appetite suppression, drowsiness, analgesia or hypotension.

9. The method of claim 7 wherein the amount administered.is 5 mg to 100 mg per day.

10. The method according to claim 9 wherein the amount administered to 40 mg to 80 mg per day.

11. The method according to claim 7 wherein the amount of S(+) fluoxetine or a pharmaceutically acceptable salt thereof is greater than approximately 99% by weight.

12. The method according to claim 7 wherein S(+) fluoxetine or a pharmaceutcally acceptable salt thereof, substantially free of its R(−) stereoisomer is administered together with a pharmaceutically acceptable carrier.

13. A method according to claim 9 wherein S(+) fluoxetine hydrochloride is administered.

* * * * *

UNITED STATES PATENT AND TRADEMARK OFFICE
CERTIFICATE OF CORRECTION

PATENT NO. : 5,104,899

DATED : April 14, 1992

INVENTOR(S) : James W. Young and Timothy J. Barberich

It is certified that error appears in the above-identified patent and that said Letters Patent is hereby corrected as shown below:

Column 3, line 53, "human,s" should be --human's--.

Column 5, line 21, "HCL/aq. ether" should be --HCl/ether--.

Column 10, line 5, the chemical structure

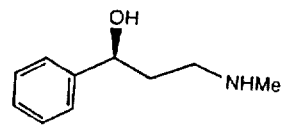

should be

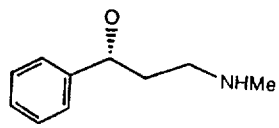

line 46, "(s)" should be --(8)--;
line 47, "2.16" should be --2.16°--;
line 48, "7.08" should be --7.08°--;

UNITED STATES PATENT AND TRADEMARK OFFICE
CERTIFICATE OF CORRECTION

PATENT NO. : 5,104,899

DATED : April 14, 1992

Page 2 of 2

INVENTOR(S) : James W. Young and Timothy J. Barberich

It is certified that error appears in the above-identified patent and that said Letters Patent is hereby corrected as shown below:

Column 12, claim 1, line 1, "physchological" should be --psychological--;
line 2, "comprisesd" should be --comprises--;
claim 4, line 13, "claim" should be --claim 1--;
claim 5 should read --The method according to claim 1 wherein S(+) fluoxetine, or a pharmaceutically acceptable salt thereof, substantially free of its R(-) stereoisomer is administered together with a pharmaceutically acceptable carrier.;
claim 6, line 23, "flouxetine" should be --fluoxetine--;
claim 9, line 35, "administered.is" should be --administered is--.

Signed and Sealed this

Thirteenth Day of July, 1993

Attest:

MICHAEL K. KIRK

Attesting Officer

Acting Commissioner of Patents and Trademarks